(12) United States Patent
Nakajima et al.

(10) Patent No.: US 11,056,238 B1
(45) Date of Patent: Jul. 6, 2021

(54) PERSONALITY BASED WELLNESS COACHING

(71) Applicant: Apple Inc., Cupertino, CA (US)

(72) Inventors: Taido L. Nakajima, San Jose, CA (US); Bryan J. James, Menlo Park, CA (US); Barker N. Bhaskaran, Fremont, CA (US)

(73) Assignee: Apple Inc., Cupertino, CA (US)

( * ) Notice: Subject to any disclaimer, the term of this patent is extended or adjusted under 35 U.S.C. 154(b) by 825 days.

(21) Appl. No.: 14/670,846

(22) Filed: Mar. 27, 2015

Related U.S. Application Data

(60) Provisional application No. 61/971,367, filed on Mar. 27, 2014.

(51) Int. Cl.
*G16H 50/30* (2018.01)

(52) U.S. Cl.
CPC .................... *G16H 50/30* (2018.01)

(58) Field of Classification Search
CPC ............................ G09B 19/003; G06F 19/3431
USPC .......................................................... 434/247
See application file for complete search history.

(56) References Cited

U.S. PATENT DOCUMENTS

| | | |
|---|---|---|
| 4,803,625 A | 2/1989 | Fu |
| 5,612,869 A | 3/1997 | Letzt et al. |
| 6,619,835 B2 | 9/2003 | Kita |
| 6,678,613 B2 * | 1/2004 | Andrews ............... G01C 21/20 342/357.75 |
| 7,172,530 B1 * | 2/2007 | Hercules ............ A63B 24/0006 482/4 |
| 7,925,525 B2 * | 4/2011 | Chin .................... G06Q 10/109 340/539.13 |
| 2005/0031096 A1 * | 2/2005 | Postrel .............. H04M 3/42229 379/88.22 |
| 2005/0171410 A1 * | 8/2005 | Hjelt ........................ A61B 5/00 600/300 |

(Continued)

FOREIGN PATENT DOCUMENTS

WO      2012/021507 A2      2/2012

OTHER PUBLICATIONS

Das, Sajal, K., et al., "Health Monitoring in an Agent-Based Smart Home by Activity Prediction," in Proc. Int'l Conf. on Smart Homes and Health Telematics (ICOST) 2004, pp. 3-14.

(Continued)

*Primary Examiner* — William D Ermlick
(74) *Attorney, Agent, or Firm* — Kilpatrick Townsend & Stockton LLP

(57) ABSTRACT

Automated wellness coaching can be based at least in part on personality characteristics of the user. A coaching system, which can include one or more electronic devices that a user might carry or wear during daily activities, can present prompts at selected times to encourage a user to engage in various wellness activities and can measure the user's responsiveness. The content of a prompt, as well as the time, place, and/or manner of presenting the prompt, can be adapted to a personality profile maintained for the user and updated over time as the user interacts with the system. The system may also include capabilities to set specific wellness goals for the user and to prompt the user to actions aimed at the goal; goals can be modified and adapted based on the user's personality profile.

18 Claims, 6 Drawing Sheets

(56) References Cited

U.S. PATENT DOCUMENTS

| | | | |
|---|---|---|---|
| 2006/0136173 A1* | 6/2006 | Case, Jr. | A63B 24/00 702/182 |
| 2006/0183980 A1 | 8/2006 | Yang | |
| 2007/0197881 A1 | 8/2007 | Wolf | |
| 2008/0061961 A1* | 3/2008 | John | A61B 5/4809 340/539.12 |
| 2008/0030772 A1 | 12/2008 | Shahrokh | |
| 2009/0076335 A1* | 3/2009 | Schwarzberg | G06F 19/3475 600/300 |
| 2009/0076842 A1* | 3/2009 | Schwarzberg | G06F 19/345 705/2 |
| 2010/0197463 A1* | 8/2010 | Haughay, Jr. | A63B 24/0062 482/8 |
| 2011/0003665 A1 | 1/2011 | Burton | |
| 2011/0050428 A1* | 3/2011 | Istoc | G16H 50/20 340/573.1 |
| 2012/0194676 A1 | 8/2012 | Laganiere | |
| 2012/0296191 A1* | 11/2012 | McGrath | A61B 5/0476 600/383 |
| 2013/0162424 A1* | 6/2013 | Treacy | G08B 21/182 340/502 |
| 2013/0293363 A1* | 11/2013 | Plymouth | G06Q 20/10 340/309.16 |
| 2014/0012117 A1* | 1/2014 | Mensinger | A61B 5/7475 600/365 |
| 2014/0052280 A1* | 2/2014 | Yuen | G06F 11/00 700/91 |
| 2014/0207373 A1* | 7/2014 | Lerenc | G01C 21/3438 701/465 |
| 2014/0270375 A1* | 9/2014 | Canavan | A63B 24/0062 382/103 |
| 2015/0080184 A1* | 3/2015 | Boyette | A63B 24/0075 482/9 |
| 2015/0106025 A1* | 4/2015 | Keller | G06Q 10/101 702/19 |
| 2015/0302726 A1* | 10/2015 | Treacy | G08B 21/182 340/502 |
| 2015/0346983 A1* | 12/2015 | Adler | G06Q 10/1093 715/772 |
| 2018/0097704 A1* | 4/2018 | Carey | H04L 41/142 |
| 2018/0101901 A1* | 4/2018 | Jones-McFadden | G06Q 40/02 |
| 2018/0204442 A1* | 7/2018 | Faaborg | G08B 6/00 |
| 2019/0371197 A1* | 12/2019 | Arnold | G06F 3/0484 |
| 2020/0098456 A1* | 3/2020 | Loscutoff | G16H 50/30 |

OTHER PUBLICATIONS

Wilson, Daniel, H., "Assistive Intelligent Environments for Automatic Health Monitoring," Sep. 2005 Doctoral Thesis, Robotics Institute, Carnegie Mellon University, Pittsburgh, PA, 185 pages.

Barger, Tracy, et al., "Health Status Monitoring Through Analysis of Behavioral Patterns," IEEE Trans. Systems, Man and Cybernetics, Jan. 2005, Part A: Systems and Humans, (35:1), pp. 22-27.

Cesta, Amedeo, et al., "Monitoring Elderly Peopel with the Robocare Domestic Environment: Interaction Synthesis and User Evaluation," Computational Intellegince, Nov. 1, 2011, vol. 27, pp. 60-82.

Buttussi, Fabio, et al., "MOPET: A context-aware and user-adaptive wearable system for fitness training," Artificial Intelligence in Medicine, 2008, vol. 42, pp. 153-163.

"Trying to Lose Weight? Get Reminder Texts Exactly When You Need 'Em," Self Magazine, [online], [retrieved on Aug. 1, 2013], retrieved from the internet <URL: http://www.self.com/blogs/flash/2013/03/trying-to-lose-weight-get-remi.html,> 7 pages.

* cited by examiner

Hi Susan, nice to meet you.
To help me get to know you, please provide some information about yourself. All items are optional Age: [        ]      Gender: [        ]

Height: [        ]    Weight: [        ]

Please indicate if you have or have had any of the following?

- [ ] Heart attack
- [ ] Stroke
- [ ] High blood pressure
- [ ] Diabetes

...

Tell me about your current habits

Sleep (hours/night): _____

Exercise frequency: _____ days/week

Exercise type:
- [ ] Running
- [ ] Walking
- [ ] Cycling
- [ ] Weightlifting

...

Finally, tell me about your goals

Lose weight (target weight = _____)

Be more active (active hours/day = _____)

...

[ DONE ]

FIG. 4

| Style/Content | Score (F, R) |
|---|---|
| Motivational | |
| Educational | |
| Supportive | |
| Reminder | |
| Social | |
| Challenging | |

| Presentation/Manner | Score (F, R) |
|---|---|
| Voice only | |
| Text only | |
| Text+Haptic | |
| Text+Sound | |
| Voice+Text | |

| Context/Time & Place | Score (F, R) |
|---|---|
| Morning prompt | |
| Afternoon prompt | |
| Evening prompt | |
| Prompt at work | |
| Prompt at home | |
| Status when prompted | |
| Status when active | |

*FIG. 5*

PERSONALITY BASED WELLNESS COACHING

CROSS-REFERENCE TO RELATED APPLICATIONS

This application claims the benefit of U.S. Provisional Application No. 61/971,367, filed Mar. 27, 2014, entitled Personality-Based Wellness Coaching," the disclosure of which is incorporated by reference herein in its entirety.

BACKGROUND

The present disclosure relates generally to personal fitness devices and in particular to a personal fitness device that provides wellness coaching.

Medical science has established that regular physical activity is important to maintaining good health. Regrettably, however, the advancement of technology has generally coincided with a reduction of physical activity. Instead of having to earn a living through physically demanding labor, many people today find that their daily routine consists largely of sitting in front of a computer or television screen, punctuated by intervals of sitting in a car in traffic. Physical activity has, for many, become another chore to be scheduled and carried out or, as is often the case, forgotten entirely.

SUMMARY

Certain embodiments of the present invention relate to systems and methods for providing automated wellness coaching based at least in part on personality characteristics of the user. A coaching system, which can include one or more mobile and/or wearable electronic devices, can present prompts at selected times to encourage a user to engage in various wellness activities such as exercising (walking, cycling, running, swimming, weightlifting, etc.), meditating, learning about healthy habits (e.g., food choices), and so on. The system can measure the user's responsiveness to various prompts. In some embodiments, the content of a prompt, as well as the time, place, and/or manner of presenting the prompt, can be adapted to a personality profile maintained for the user and updated over time as the user interacts with the system. In some embodiments, the system can also include capabilities to set specific wellness goals for the user and to prompt the user to actions aimed at the goal; goals can be modified and adapted based on the user's personality profile.

The following detailed description together with the accompanying drawings will provide a better understanding of the nature and advantages of the present invention.

BRIEF DESCRIPTION OF THE DRAWINGS

FIG. 4 illustrates one example of a baseline data interface according to an embodiment of the present invention.

FIG. 5 illustrates elements of a personality profile according to an embodiment of the present invention.

DETAILED DESCRIPTION

Figure 1:
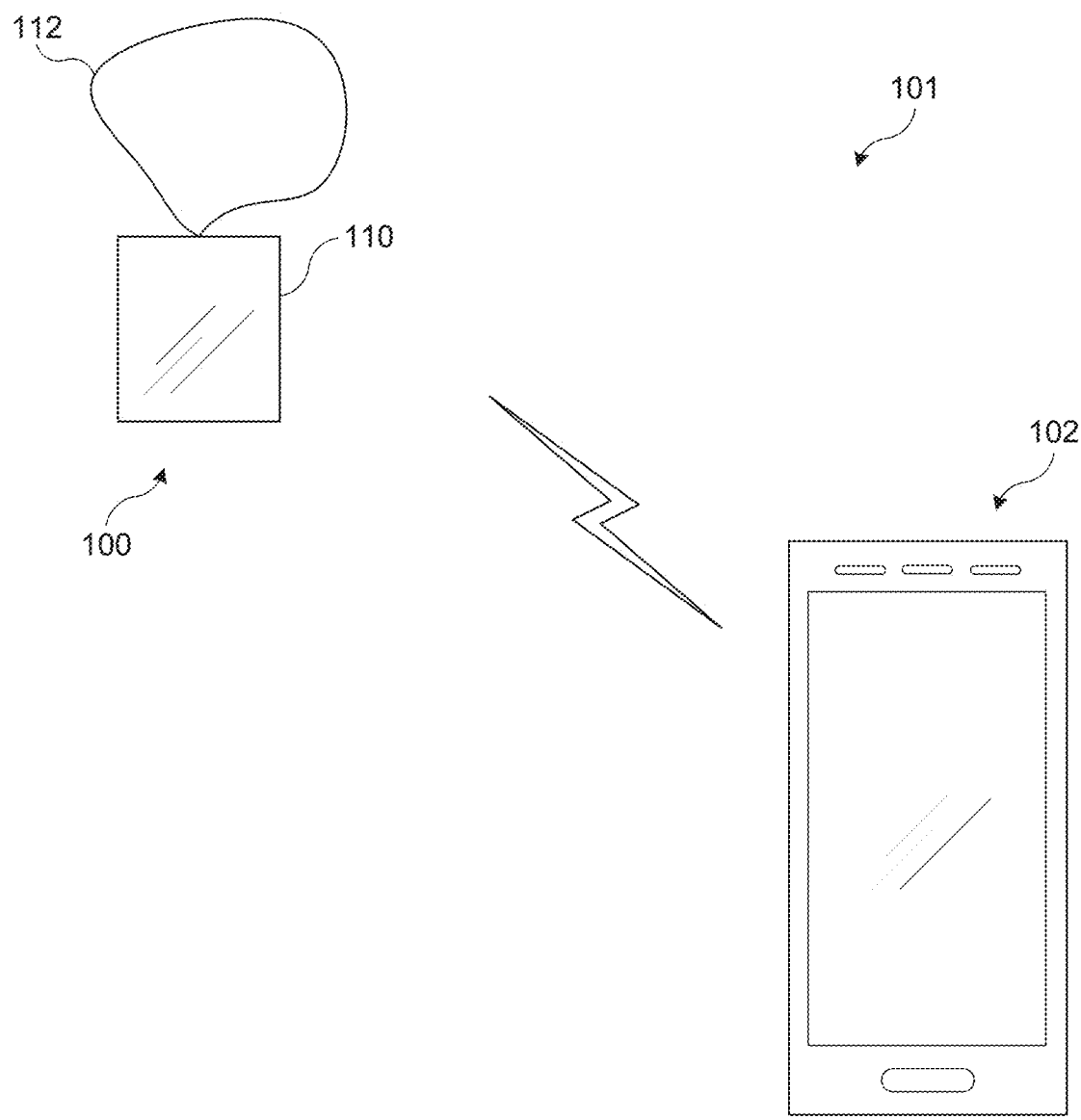
FIG. 1 shows an electronic coaching system according to an embodiment of the present invention.

Certain embodiments of the present invention relate to systems and methods for providing automated wellness coaching based at least in part on personality characteristics of the user. A coaching system, which can include one or more mobile and/or wearable electronic devices, can present prompts at selected times to encourage a user to engage in various wellness activities such as exercising (walking, cycling, running, swimming, weightlifting, etc.), meditating, learning about healthy habits (e.g., food choices), and so on. In some embodiments, the content of a prompt, as well as the time, place, and/or manner of presenting the prompt, can be adapted to the user's personality over time.

In some embodiments, a coaching system can determine an initial personality profile for the user based on a setup process in which the user is guided through a series of questions, answers to which can be optional. Based on whether and how the user answers various questions, the coaching system can infer, for instance, whether the user is skeptical toward coaching or eager to try it or somewhere in between. Thereafter, by deploying coaching tools (including activity prompts and/or other messages) and monitoring whether and how the user responds to the tools, the coaching system can refine the user's personality profile and adjust for changes over time, such as an initially skeptical user becoming more receptive.

The specific content of prompts that are presented can be selected based on information gleaned about a user's personality through repeated interactions with the coaching system. For instance, the coaching system may be able to present prompts reflective of a range of coaching "styles," such as a motivational style (e.g., "walking makes you feel good"), an educational style (e.g., "people who walk more enjoy reduced risk of a certain disease"), a supportive style (e.g., "you can take time for a walk"), a reminder style (e.g., "take a walk today"), a social style (alerting friends of the plan to walk), and/or a goal-oriented style (e.g., "try to walk for fifteen minutes every day this week"). Different users will respond differently to different styles, and by tracking the user's responses to various prompts over time, the coaching system can identify a style or combination of styles that is effective for a given user.

In some embodiments, the times and places when prompts are presented can be selected dynamically by the coaching system based on information about the user's current context, schedule, and/or past patterns of responsiveness to prompts. For example, on a given day, a user's coaching system might determine, based on an activity history, that the user should take a walk for fifteen minutes and that the user generally prefers to walk in the afternoon. The coaching system can access the user's electronic calendar and identify a free block of time in the afternoon during which the user could take a walk. The specific timing of presenting a prompt to take a walk at that time can be selected based in part on a pattern of responsiveness of the user to previous prompts. For instance, if the user has frequently responded right away, the coaching system can issue the activity prompt shortly before or at the beginning of the free block of time. If the user is known to be more responsive to prompts given well in advance, the prompt can be issued prior to the free block of time, for example, in the morning when the user first arrives at work and is planning out her day. The coaching system can also adjust the presentation of prompts based on information about the user's current location and activity. For instance, if the user is already walking, the coaching system can suppress a prompt to take a walk, or if the user is in a meeting, the coaching system can suppress the prompt.

The manner of presenting prompts can also be dependent on the user's personality and/or responsiveness to different modes of presentation. For instance, a prompt can be presented using speech (e.g., synthesized or prerecorded speech), text (e.g., an onscreen message), alert sounds (e.g., a beep or fragment of music), haptic outputs (e.g., vibrations of a device), or some combination of these methods and/or other methods of presenting information to a user. The coaching system can monitor the user's responsiveness to various manners of presenting prompts and can adapt the presentation manner based on the user's responsiveness. In some instances, a user may be more responsive to different presentation manners for different types of prompts, and manner of presentation can also be correlated with other aspects of the prompt (e.g., content and/or timing).

In some embodiments, the coaching system can also facilitate goal-setting for the user. For example, based on initial information provided by the user and/or monitoring of the user's activity over time, the coaching system can determine the user's current activity level and select a goal that will improve on the current level. Goals can be defined as desired. For instance, in some embodiments, the system can determine the number of minutes the user spends walking around or doing other physical activity on a daily basis and can determine that the user should increase that level by a certain amount (e.g., from ten minutes a day to thirty minutes a day) over a period of time (e.g., the next month). Goals can also be based on distance (e.g., if the user wants to run a marathon, the system can set training goals building toward being able to run marathon distance), step count, or any other measurable parameter of performance. As with other aspects of coaching, goal-setting can be adaptive based on the user's activity patterns, indicated preferences, and/or responsiveness to coaching over time.

In addition to prompts for specific activities, the coaching system can also deploy other coaching tools such as supportive or motivational messages while the user is doing an activity, educational information made available at the user's convenience, tracking tools that show the user's progress over time (e.g., relative to a goal). Like activity prompts, other coaching tools can be deployed based on information about the user's personality, schedule, current location, and so on.

In some embodiments, a coaching system can be implemented using one or more personal electronic devices that a user can carry and/or wear. For example, FIG. 1 shows an electronic coaching system 101 that includes a wearable device 100 communicating wirelessly with a host device 102 according to an embodiment of the present invention.

Wearable device 100 can be, for example, a necklace, a wristband, a bracelet, a watch, eyeglasses or other eyewear, a headband, a ring, etc. Wearable device 100 can include an active component 110 and an attachment member 112. Active component 110 can include various physiological sensors, motion sensors, and/or other environmental sensors; user input devices (e.g., control buttons, knobs, and/or dials; touch sensor or touch screen; microphone); and/or user output devices (e.g., display, speakers, haptic devices). In addition, active component 110 can include a communication interface, such as a wireless communication interface, that supports exchange of information between wearable device 100 and host device 102.

Attachment member 112 can allow the user to wear device 100 attached to the user's person or clothing. For example, attachment member 112 can include a strap or chain to allow attachment to the user's wrist or wearing around the user's neck, an ear piece to support wearing of device 100 on the user's head, a clip or pin to support attachment of device 100 to an article of clothing that the user wears, and so on. In some embodiments, attachment member 112 can also incorporate active electronic components such as sensors, user interface components, data communication interfaces, and the like.

In some embodiments, active component 110 can determine whether wearable device 100 is being worn at any given time, e.g., based on sensor data and/or signals from attachment member 112. Wearable device 100 can operate differently depending on whether it is currently being worn or not. For example, wearable device 100 can inactivate various user interface and/or RF interface components when it is not being worn. In addition, in some embodiments, wearable device 100 can notify host device 102 when a user puts on or takes off wearable device 100.

Host device 102 can be any device that communicates with wearable device 100. In FIG. 1, host device 102 is shown as a smart phone; however, other host devices can be substituted, such as a tablet computer, a media player, any type of mobile phone, a laptop or desktop computer, or the like. Host device 102 can communicate wirelessly with wearable device 100, e.g., using protocols such as Bluetooth or Wi-Fi. In some embodiments, wearable device 100 can include an electrical connector that can be used to provide a wired connection to host device 102 and/or to other devices, e.g., by using suitable cables. For example, connector 110 can be used to connect to a power supply to charge an onboard battery of wearable device 100.

In some embodiments, wearable device 100 and host device 102 can interoperate to enhance functionality available on host device 102. For example, wearable device 100 and host device 102 can establish a pairing using a wireless communication technology such as Bluetooth. While the devices are paired, host device 102 can send notifications of selected events (e.g., a trigger for a coaching prompt) to wearable device 100, and wearable device 100 can present corresponding alerts or prompts to the user. Wearable device 100 can also provide an input interface via which a user can input information, e.g., dismissing a prompt or indicating start or end of a workout, etc. In some embodiments, wearable device 100 can provide sensor data (e.g., physiological sensor data and/or environmental sensor data) to host device 102, and host device 102 can use the sensor data to implement coaching functionality as described herein (e.g., setting goals, assessing user performance of an activity and/or progress toward a goal, etc.).

It will be appreciated that wearable device 100 and host device 102 are illustrative and that variations and modifications are possible. In some embodiments, coaching system 101 can incorporate other devices in addition to or instead of those shown. For example, some embodiments can include a desktop or laptop computer that can communicate with other devices in the system, e.g., with wearable device 100 and/or host device 102. In some embodiments, host device 102 can be a desktop or laptop computer, tablet, mobile phone, or the like, and there can be multiple host devices. In other embodiments, coaching system 101 can be implemented as a single device such as wearable device 100 or host device 102, and multiple interoperating devices are not required.

Accordingly, a "coaching system" as used herein is to be understood as including a single device that operates and/or a combination of devices that interoperate to perform coaching operations as described herein. To avoid requiring the user to be in any particular location to receive coaching, a coaching system can include at least one device that the user can carry or wear while going about daily activities, such as a mobile phone or wearable device.

Figure 2:
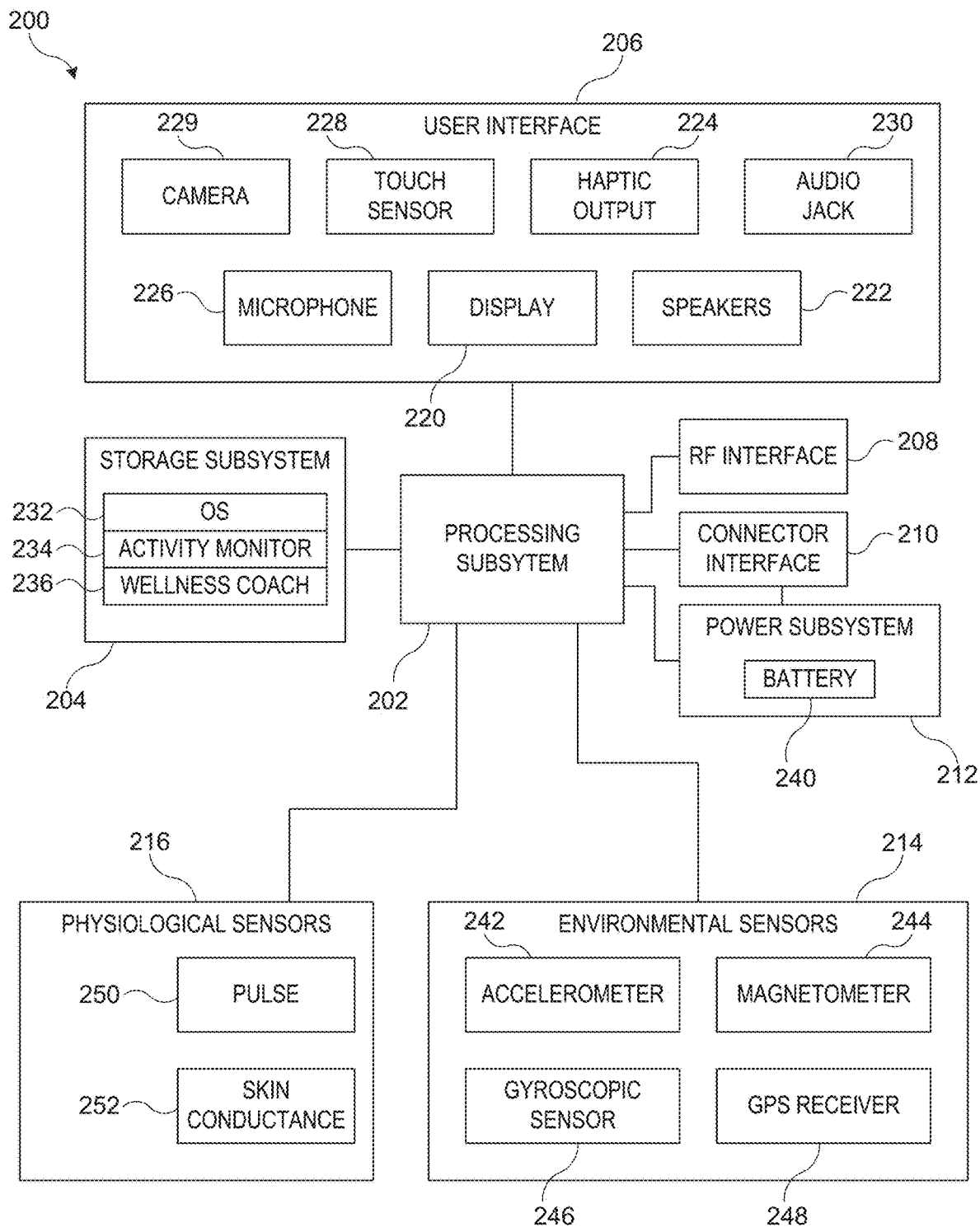
FIG. 2 is a simplified block diagram of a coaching system according to an embodiment of the present invention.

FIG. 2 is a simplified block diagram of a coaching system 200 according to an embodiment of the present invention. In some embodiments, various blocks of coaching system 200 can be implemented in host device 102 and/or wearable device 100 of FIG. 1. Coaching system 200 can include processing subsystem 202, storage subsystem 204, user interface 206, RF interface 208, connector interface 210, environmental sensors 214, and physiological sensors 216. Coaching system 200 can also include other components (not explicitly shown).

Storage subsystem 204 can be implemented, e.g., using magnetic storage media, flash memory, other semiconductor memory (e.g., DRAM, SRAM), or any other non-transitory storage medium, or a combination of media, and can include volatile and/or non-volatile media. In some embodiments, storage subsystem 204 can store media items such as audio files, video files, image or artwork files; information about a user's contacts (names, addresses, phone numbers, etc.); information about a user's calendar (e.g., scheduled appointments and events; notes; and/or other types of information, examples of which are described below. In some embodiments, storage subsystem 204 can also store one or more application programs to be executed by processing subsystem 210 (e.g., personal information management programs, fitness and/or wellness related programs, etc.).

User interface 206 can include any combination of input and output devices. A user can operate input devices of user interface 206 to invoke the functionality of coaching system 200 and can view, hear, and/or otherwise experience output from coaching system 200 via output devices of user interface 206.

Examples of output devices include display 220, speakers 222, and haptic output generator 224. Display 220 can be implemented using compact display technologies, e.g., LCD (liquid crystal display), LED (light-emitting diode), OLED (organic light-emitting diode), or the like. In some embodiments, display 220 can incorporate a flexible display element or curved-glass display element, allowing coaching system 200 to conform to a desired shape. One or more speakers 222 can be provided using small-form-factor speaker technologies, including any technology capable of converting electronic signals into audible sound waves. In some embodiments, speakers 222 can be used to produce tones (e.g., beeping or ringing) and can but need not be capable of reproducing sounds such as speech or music with any particular degree of fidelity. Haptic output generator 224 can be, e.g., a device that converts electronic signals into vibrations; in some embodiments, the vibrations can be strong enough to be felt by a user wearing coaching system 200 but not so strong as to produce distinct sounds.

Examples of input devices include microphone 226, touch sensor 228, and camera 229. Microphone 226 can include any device that converts sound waves into electronic signals. In some embodiments, microphone 226 can be sufficiently sensitive to provide a representation of specific words spoken by a user; in other embodiments, microphone 226 can be usable to provide indications of general ambient sound levels without necessarily providing a high-quality electronic representation of specific sounds.

Touch sensor 228 can include, e.g., a capacitive sensor array with the ability to localize contacts to a particular point or region on the surface of the sensor and in some instances, the ability to distinguish multiple simultaneous contacts. In some embodiments, touch sensor 228 can be overlaid over display 220 to provide a touchscreen interface (e.g., touchscreen interface 105 of FIG. 1), and processing subsystem 202 can translate touch events (including taps and/or other gestures made with one or more contacts) into specific user inputs depending on what is currently displayed on display 220.

Camera 229 can include, e.g., a compact digital camera that includes an image sensor such as a CMOS sensor and optical components (e.g. lenses) arranged to focus an image onto the image sensor, along with control logic operable to use the imaging components to capture and store still and/or video images. Images can be stored, e.g., in storage subsystem 204 and/or transmitted by coaching system 200 to other devices for storage. Depending on implementation, the optical components can provide fixed focal distance or variable focal distance; in the latter case, autofocus can be provided. Zero, one, or more cameras can be provided, depending on implementation.

In some embodiments, user interface 206 can provide output to and/or receive input from an auxiliary device such as a headset. For example, audio jack 230 can connect via an audio cable (e.g., a standard 2.5-mm or 3.5-mm audio cable) to an auxiliary device. Audio jack 230 can include input and/or output paths. Accordingly, audio jack 230 can provide audio to the auxiliary device and/or receive audio from the auxiliary device. In some embodiments, a wireless connection interface can be used to communicate with an auxiliary device.

Processing subsystem 202 can be implemented as one or more integrated circuits, e.g., one or more single-core or multi-core microprocessors or microcontrollers, examples of which are known in the art. In operation, processing system 202 can control the operation of coaching system 200. In various embodiments, processing subsystem 202 can execute a variety of programs in response to program code and can maintain multiple concurrently executing programs or processes. At any given time, some or all of the program code to be executed can be resident in processing subsystem 210 and/or in storage media such as storage subsystem 204.

Through suitable programming, processing subsystem 202 can provide various functionality for coaching system 200. For example, in some embodiments, processing subsystem 202 can execute an operating system (OS) 232 and various applications (also referred to as apps) for interfacing with a host device, such as an activity monitoring app 234 and/or a wellness coaching app 236. For example, activity monitoring app 234 can collect and store activity-related information such as heart rate, step count, or the like, and such information can be presented to a user, e.g., via display 220. Similarly, wellness coaching app 236 can use stored data to select coaching prompts to present to the user. Examples of such processes are described below. In some embodiments, activity monitoring app 234 and/or wellness coaching app 236 executing on a particular device within a coaching system can generate messages to another device within the coaching system and/or receive messages and/or program code updates from another device.

RF (radio frequency) interface 208 can allow a device in a coaching system to communicate wirelessly with various other devices, which may or may not be part of the same coaching system. RF interface 208 can include RF transceiver components such as an antenna and supporting circuitry to enable data communication over a wireless medium, e.g., using Wi-Fi (IEEE 802.11 family standards), Bluetooth® (a family of standards promulgated by Bluetooth SIG, Inc.), or other protocols for wireless data communication. RF interface 208 can be implemented using a combination of hardware (e.g., driver circuits, antennas, modulators/demodulators, encoders/decoders, and other analog and/or digital signal processing circuits) and software components. In some embodiments, RF interface 208 can provide near-field communication ("NFC") capability, e.g., implementing the ISO/IEC 18092 standards or the like; NFC can support wireless data exchange between devices over a very short range (e.g., 20 centimeters or less). Multiple different wireless communication protocols and associated hardware can be incorporated into RF interface 208.

Connector interface 210 can allow a device in a coaching system to communicate with various other devices (which may or may not be part of the same coaching system) via a wired communication path, e.g., using Universal Serial Bus (USB), universal asynchronous receiver/transmitter (UART), or other protocols for wired data communication. In some embodiments, connector interface 210 can provide a power port, allowing coaching system 200 to receive power, e.g., to charge an internal battery. For example, connector interface 210 can include a connector such as a mini-USB connector or a custom connector, as well as supporting circuitry.

In some embodiments, connector interface 210 and/or RF interface 208 can be used to support synchronization operations in which data is transferred between devices within a coaching system and/or other devices. For example, as described below, a user can customize certain information for coaching system 200 (e.g., providing wellness-related personal information to be used by activity monitor 234 and/or wellness coach 236 as described below). While any user interface 206 in any device of a coaching system can support data-entry operations, a user may find it more convenient to enter data using a device such as a tablet or laptop computer that has a larger interface (e.g., including a real or virtual alphanumeric keyboard), then transfer the data to other devices of coaching system 200 via a synchronization operation. Synchronization operations can also be used to load and/or update other types of data in storage subsystem 204, such as media items, application programs, and/or operating system programs, as well as to transfer data (e.g., activity data gathered by activity monitor 234) from storage subsystem 204 to other devices. Synchronization operations can be performed in response to an explicit user request and/or automatically, e.g., when particular synchronized devices resume communication with each other, or in response to a device receiving an update to its copy of synchronized information.

Environmental sensors 214 can include various electronic, mechanical, electromechanical, optical, or other devices that provide information related to external conditions around coaching system 200. Sensors 214 in some embodiments can provide digital signals to processing subsystem 202, e.g., on a streaming basis or in response to polling by processing subsystem 202 as desired. Any type and combination of environmental sensors can be used; shown by way of example are accelerometer 242, a magnetometer 244, a gyroscope 246, and a GPS receiver 248.

Some environmental sensors can provide information about the location and/or motion of coaching system 200 or a component device thereof. For example, accelerometer 242 can sense acceleration (relative to freefall) along one or more axes, e.g., using piezoelectric or other components in conjunction with associated electronics to produce a signal. Magnetometer 244 can sense an ambient magnetic field (e.g., Earth's magnetic field) and generate a corresponding electrical signal, which can be interpreted as a compass direction. Gyroscopic sensor 246 can sense rotational motion in one or more directions, e.g., using one or more MEMS (micro-electro-mechanical systems) gyroscopes and related control and sensing circuitry. Global Positioning System (GPS) receiver 248 can determine geographic location based on signals received from GPS satellites.

Other sensors can also be included in addition to or instead of these examples. For example, a sound sensor can incorporate microphone 226 together with associated circuitry and/or program code to determine, e.g., a decibel level of ambient sound. Temperature sensors, proximity sensors, ambient light sensors, or the like can also be included.

Physiological sensors 216 can include various electronic, mechanical, electromechanical, optical, chemical or other devices that provide information about the physiological status of a user. For instance, a pulse sensor 250 can detect a user's pulse based on pressure changes against a pressure sensor, electrical impulses, or the like. In some embodiments, pulse sensor 250 can include an optical sensor and can provide pulse oximetry data (both heart rate and oxygen content of the blood). A skin conductance sensor 252 can measure changes in the user's skin conductance that may indicate sweating, stress, or the like. Other types of sensors can also be used, including temperature sensors, ECG sensors, and so on. In some embodiments, physiological sensors 216 can be disposed in wearable component devices of a coaching system (e.g., in wearable device 100 of FIG. 1).

It will be appreciated that coaching system 200 is illustrative and that variations and modifications are possible. For example, coaching system 200 can include any types and combination of sensors and in some instances can include multiple sensors of a given type; different sensors can be disposed in different discrete devices of a single coaching system.

In various embodiments, a user interface can include any combination of any or all of the components described above, as well as other components not expressly described. For example, in some embodiments, the user interface can include, e.g., just a touchscreen, or a touchscreen and a speaker, or a touchscreen and a haptic device. Devices can have wireless (e.g., RF) and/or wired interfaces as desired. Devices can also include other components not shown in FIG. 2, such as power sources (e.g., batteries, solar cells) and/or power management circuitry or control logic, etc.

Further, while coaching system 200 is described with reference to particular blocks that can be implemented in a single user device, it is to be understood that these blocks and arrangements are defined for convenience of description and are not intended to imply a particular physical arrangement of component parts. Further, the blocks need not correspond to physically distinct components. It is also to be understood that coaching system 200 can be implemented using multiple devices, and some blocks may be implemented in one device while other blocks are implemented in another device (or not at all); implementations of a single block of FIG. 2 can also be present in multiple devices within a single coaching system (e.g., multiple devices may each have a touch screen, a speaker, a processor, etc.). Blocks can be configured to perform various operations, e.g., by programming a processor or providing appropriate control circuitry, and various blocks might or might not be reconfigurable depending on how the initial configuration is obtained. In some embodiments, program code can be implemented on multiple user devices that interoperate; accordingly, operations described herein as being executed by a single application or device can be executed using different, cooperating devices in a multi-device coaching system. Embodiments of the present invention can be realized in a variety of apparatus including electronic devices implemented using any combination of circuitry and software.

Where a coaching system includes multiple devices (e.g., a host device and a wearable device), communication between or among these devices can be implemented according to any communication protocol (or combination of protocols) that the devices are programmed or otherwise configured to use. In some instances, standard protocols such as Bluetooth protocols can be used. In some instances, a custom message format and syntax (including, e.g., a set of rules for interpreting particular bytes or sequences of bytes in a digital data transmission) can be defined, and messages can be transmitted using standard serial protocols such as a virtual serial port defined in certain Bluetooth standards. Embodiments of the invention are not limited to particular protocols, and those skilled in the art with access to the present teachings will recognize that numerous protocols can be used.

In some embodiments, coaching system 200 can provide wellness monitoring, e.g., by monitoring a user's activities and/or vital signs on an ongoing basis. For example, activity monitoring application 234 of FIG. 2 can continuously run as a background process while the user is wearing or carrying a component device of coaching system 200 (e.g., wearable device 100 of FIG. 1). Activity monitoring application 234 can collect and/or analyze data (signals) from physiological sensors 216 and/or environmental sensors 214. For instance, activity monitoring application 234 can use data from accelerometer 242 and/or GPS receiver 248 to determine whether the user is engaged in a physical activity such as walking, running, cycling, swimming, or the like. Application 234 can further analyze the data to track the user's performance, e.g., distance and/or number of strides walked or run. In some embodiments, application 234 can also use physiological sensor data to facilitate detecting physical activity (e.g., elevated heart rate) and/or to record data related to the physical activity (e.g., heart rate at various times during a workout and/or while at rest). In some embodiments, activity monitoring application 234 can present data to the user on a wearable device (e.g., wearable device 100 of FIG. 1).

In conjunction with wellness monitoring, coaching system 200 can provide automated coaching to encourage the user to develop habits that facilitate wellness. For example, wellness coaching application 236 of FIG. 2 can run as a background process when coaching system 200 is in use (e.g., while the user is wearing or carrying coaching system 200 or a component device thereof). Wellness coaching application 236 can provide prompts, feedback, and/or other information (generally referred to herein as "coaching") intended to help the user develop or improve on wellness-related behaviors and/or habits. For instance, the user can be coached to increase the frequency and/or duration of physical activity, with the increase being gradual over time. The user can also be coached on other aspects of wellness, such as stress reduction, sleep, and/or healthy eating habits. The coaching can be based in part on information obtained from activity monitoring application 234. In some embodiments, the coaching can be adaptive, with the content of coaching messages presented to the user (e.g., prompts, feedback, or other information), as well as the time, place and manner of presentation, being determined based on past patterns of user behavior, including the user's responses to previous coaching. Thus, much like a human coach, an automated wellness coach provided by application 236 can adapt its coaching style over time toward an optimal style for a given user. (In this context, an "optimal" style is one that produces a relatively high level of responsiveness by the user to coaching prompts as compared to the same user's responsiveness to other styles.)

Figure 3:
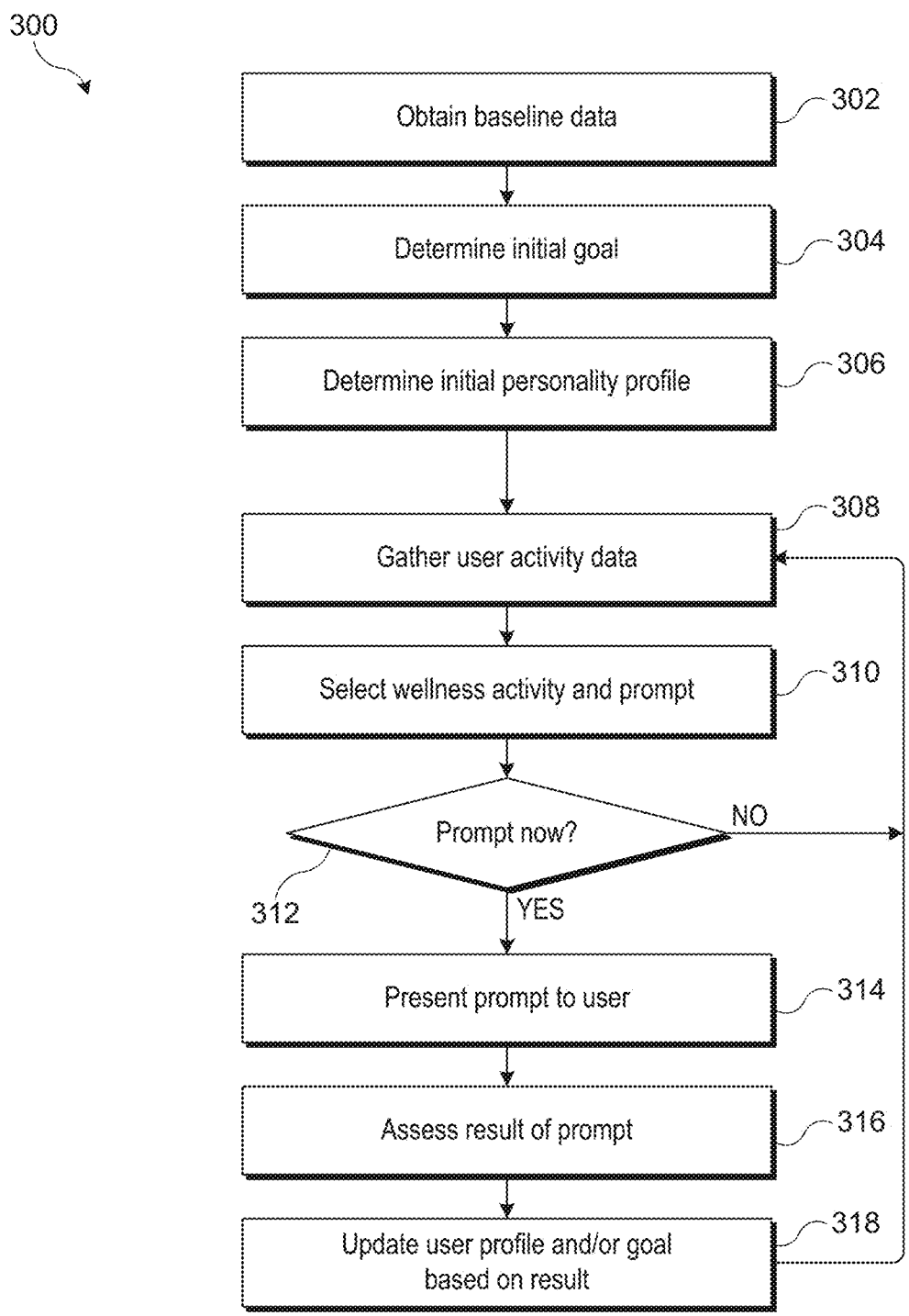
FIG. 3 is a flowchart of an adaptive coaching process according to an embodiment of the present invention.

FIG. 3 is a flowchart of an adaptive coaching process 300 according to an embodiment of the present invention. Process 300 can be implemented, e.g., in coaching application 236 of FIG. 2. In some embodiments, aspects of process 300 can be implemented in a wearable device (e.g., device 100 of FIG. 1) while other aspects are implemented in another device (e.g., host device 100 of FIG. 1) that is also part of coaching system 200.

Adaptive coaching process 300 can begin by establishing a baseline coaching behavior. For example, when the user first chooses to activate coaching system 200, process 300 can obtain baseline data for the user at block 302. For example, the user can be prompted to enter basic information such as height, weight, gender, and age. The user may also be prompted to provide other information about her fitness history and/or current condition (e.g., whether she has various health issues that may affect development of a wellness plan, whether her current lifestyle is active or sedentary), as well as information about general or specific goals the user might have (e.g., be more active, lose weight, etc.).

In some embodiments, obtaining baseline data can be performed via a graphical user interface. FIG. 4 illustrates one example of a baseline data interface 400 according to an embodiment of the present invention. Interface 400 can be a graphical user interface, and the user can enter data by checking or populating various boxes and underlined areas (e.g., as shown at 402, 404, 406). The user can choose how much or little of the requested information to provide. Done button 408 can be selected when the user is finished entering information. It is to be understood that interface 400 is illustrative and that variations and modifications are possible. The specific set of questions and/or response options can be different from those shown, and questions can be arranged as desired. In some embodiments, questions can be presented in a series of interlinked interface screens so that only a subset of the questions is presented at a given time, and the user can navigate among the screens as desired.

Referring again to FIG. 3, at block 304, process 300 can determine an initial goal for the user based on the information entered at block 302. If the user has specified a goal at block 302, the user-specified goal can be selected as the initial goal or used as the basis for selecting a related initial goal. For instance, if the user specifies a long-term goal such as "run a marathon," an initial goal might be to run two miles. If the user specifies a vague goal such as "be more active," an initial goal might be to spend fifteen minutes a day walking or doing other physical activity. In some embodiments, determining an initial goal at block 304 can be done interactively; for instance, if the user indicates a goal of running a marathon, block 304 can include asking further questions about the user's current running activity and performance (e.g., whether the user runs at all, and if so how often, how far, and/or how fast). In some embodiments, block 304 can include presenting a proposed goal to the user and asking the user to accept or revise the proposal.

In some instances, a user may provide little or no baseline data at block 302. Where this is the case, the initial goal at block 304 can be to assess the user's current activity level and/or fitness. Regardless of the initial selected goal, process 300 can subsequently set a different goal, as described below.

At block 306, process 300 can determine an initial personality profile for the user. As used herein, a "personality profile" refers generally to an assessment of the likelihood that a user will be responsive to particular coaching content and/or to coaching content presented at a particular time, place, and manner. In some embodiments, the personality profile can also include other data accumulated over time related to the user's pattern of responding or not responding to coaching.

FIG. 5 illustrates elements of a personality profile according to an embodiment of the present invention. In this example, the profile includes a number of different dimensions, corresponding to different characteristics (including content, time, place and manner) of a coaching prompt. A score is determined for each dimension of the profile. For instance, the score in each dimension can include one or more numerical metric such as frequency (F), which represents the percentage of prompts having the given characteristic that a user has responded to, and/or correlation (R), which represents the percentage of all prompts the user responded to that had the given characteristic. Other scoring metrics can also be used.

Table 502 includes characteristics related to coaching style. As used herein, a coaching style is primarily related to the content of prompts and can but need not correlate with other characteristics such as time, place and manner of presenting prompts. In one embodiment, the coaching styles can include motivational, educational, supportive, reminder, social, and challenging styles. For example, a motivational style can include presenting a reason why the user would want to take a suggested action; a motivational coaching prompt might say, e.g., "Taking a walk now might help you relax and focus better." An educational style can include factual information to help the user learn more about a suggested action or a current activity; an educational prompt might say, e.g., "A new study shows that a daily walk reduces the risk of heart disease by x percent" or (during a workout) "Your heart rate is currently below your target zone." A supportive style can include presenting words of encouragement to continue an activity; a supportive coaching prompt might say, e.g., "You've taken a walk every day so far this week; keep it up." A reminder style can include simply telling the user to do something; a reminder prompt might say, e.g., "Take a walk at 4 pm today." A social style can include sharing information about the user's activity with others (or vice versa); a social prompt might say, e.g., "Your friend Amber walked a mile today" or invite the user to share workout information through a social medium. In some embodiments, social-style coaching can include scheduling activities jointly with other users. Examples are described below. A challenging style can include setting a specific target for the activity; a challenging prompt might say, e.g., "Walk a mile today!"

In some embodiments, coaching application 236 can include a menu of different possible prompts for a given activity, with different prompts corresponding to different coaching styles. As described below, when presenting a coaching prompt, coaching application 236 can select a style for the prompt and/or the specific content of the prompt based at least in part on the user's personality profile as reflected in table 502.

In addition to selection of content, selection of the time, place, and manner of presenting a prompt can be based on or influenced by the user personality profile. For instance, table 504 can include characteristics related to the manner of presentation of the prompt. In this example, prompts can be presented using voice (e.g., synthesized or prerecorded speech) and/or text (e.g., words appearing on the display). The prompt can be accompanied by haptic (e.g., vibration) and/or sound (e.g., a beep) elements to attract the user's attention. In some embodiments, user responsiveness to various manners of presentation can be monitored over time to determine responsiveness scores. Table 504 can then be used to select a manner of presentation for the next prompt. It should be noted that the presentation manner can be selected independently of the content of the prompt. In some embodiments, selection of a presentation manner can also depend on other factors, such as whether the device that will present the prompt is currently in a silent mode; when the device is in silent mode, the selected presentation mode can be constrained accordingly (e.g., text only or text-plus-haptic). Other manners of presenting prompts or information can also be used, such as animations, images, musical presentations, etc.

Table 506 can include context-related characteristics related to the time and/or place of presentation of a prompt and/or the time and/or place at which an activity is performed. For example, prompts can be presented at different times of day, and separate responsiveness scores can be maintained for different blocks of time (e.g., a score for each hour or for larger blocks such as morning, afternoon, evening). The user may be in different locations when a prompt is received and/or when an activity is performed, and if the coaching system is location-aware (e.g., via GPS or the like), separate scores can be maintained for various locations the user regularly visits (e.g., home, work, driving, etc.). The user's context can also include a status indicative of what the user is doing. For instance, if the coaching system has access to the user's calendar, the system may be able to determine whether a user is currently in a meeting or otherwise engaged. As another example of a context-related characteristic, information from activity monitoring application 234 can be used to determine what the user is doing at a given time (e.g., sitting still, walking, sleeping), and the user activity at the time of the prompt can be a characteristic that is tracked in personality profile 500.

When the coaching system is in use, scores in any dimension can be computed by generating various prompts and assessing user responsiveness (assessing responsiveness is described below). For instance, if a motivational prompt (content) is presented as voice-only (manner) in the morning (time) when the user is at work (place), scores for each of those characteristics or dimensions can be updated based on whether the user responds or does not respond to the prompt. In some embodiments, scores for a given characteristic or dimension can be computed based on a set of up to some maximum number N of most recent prompts or for all prompts within a given period of time (e.g., within the last month). The score can be time-weighted such that more recent events have a stronger influence on the score and sufficiently old events have no influence.

It will be appreciated that the personality profile of FIG. 5 is illustrative and that variations and modifications are possible. Any combination of dimensions or characteristics of a coaching prompt can be analyzed and scored, and the particular scoring system and scoring metric(s) can be varied as desired.

Referring again to FIG. 3, at block 306, a personality profile such as profile 500 of FIG. 5 can be initialized based on a set of default scores. In some embodiments, the same default scores are used for all users. The default scores can give relatively equal scores across all dimensions; as described below, this can result in the system trying a variety of prompts. Over time, as the user responds (or doesn't respond), patterns can emerge indicative of the user's preferred coaching approach.

In other embodiments, the initial scores can be determined based at least in part on the baseline data from block 302. For example, users who indicate specific goals may be more responsive to a challenge-based coaching style than users who don't indicate any goals. As another example, the amount of baseline data provided by the user can be indicative of the user's preferences. For instance, a user who chooses to provide little or none of the information requested in FIG. 4 may be classified as being skeptical of the coaching application, and the initial coaching-style scores might be weighted in favor of educational and/or supportive styles. A user who chooses to provide extensive information may be classified as enthusiastic, and the initial coaching-style scores might be weighted in favor of motivational and/or challenge-based styles.

Once the initial user information is established, process 300 can begin gathering user activity data at block 308. This data gathering can be ongoing. In some embodiments, activity data gathering can rely on activity monitoring application 234 (which can incorporate data from various sensors of the coaching system) and can include determining whether the user is engaged in activity (and if so what type of activity), measuring physiological responses of the user, and so on. Activity data can also be gathered from other sources, such as a user's calendar, which may indicate, e.g., when a wellness activity such as a workout or meditation is scheduled. In some embodiments, the user may also be able to report activity via a user interface, e.g., on wearable device 100 and/or host device 102 of FIG. 1. Activity data gathered at block 308 can be added to a user profile maintained for the user. This user profile can include a personality profile as described above as well as data about the user's current activity level, trends in activity level over time, length of time the user has been working with the coaching system, activity patterns (e.g., when and for how long does a user do an activity), vital signs monitored over time, and so on. The user profile can also include information related to the user's responsiveness to coaching prompts, such as a typical time between prompt and response.

At block 310, process 300 can select a wellness activity and a prompt for that activity. The selection can be driven by a heuristic algorithm that takes into account the user profile (including both the personality profile and the activity profile), the current goal (e.g., as determined at block 304), and the user's current context. For example, based on the user's current goal and recent activity data, process 300 may determine that the user should engage in a particular activity in the near future (e.g., walk around the block this afternoon). A prompt for taking a walk can be selected from a menu of prompts corresponding to different coaching styles, e.g., based on the personality profile.

At block 312, process 300 can determine whether to present the selected prompt at the present time. This determination can be driven by a heuristic algorithm that takes into account the user's current context and context-related aspects of the user's personality profile. For instance, if the user is most responsive to prompts in the afternoon, process 300 can determine not to present the prompt if it is currently morning. If the user's calendar (part of the user's context) indicates that the user is in a meeting, process 300 can determine to defer until the meeting is over. If process 300 determines not to present a prompt, process 300 can continue to gather data and/or select an activity and prompt until such time as block 312 results in a determination to present a prompt.

It should be noted that some selected activities might never result in presenting a prompt. For instance, the user may do the activity before block 312 results in a determination to present a prompt to do it. As another example, a selected activity might be replaced by another activity as the user's context changes; for instance, if the user's stress level increases above some threshold (e.g., as determined by physiological sensors), a weightlifting session might be replaced with a selection of an activity that is more relaxing to the user. In some embodiments, the coaching system can determine which activities are relaxing for a particular user over time, e.g., by monitoring the user's physiological responses during and after various activities. For instance, changes in heart rate variability may be indicative of changes in stress level.

It should also be noted that delaying presentation of a prompt at block 312 can result in eventual selection of a different prompt at block 310, even if the selected activity remains the same. For example, it may be that a particular user's personality profile indicates that she is more responsive to motivational prompts in the morning and to challenge-based prompts in the afternoon. If a prompt is delayed until afternoon (e.g., because the user's calendar indicates that she is in meetings all morning), the prompt may be changed appropriately.

At block 314, a prompt can be presented to the user. As indicated above, various manners of presentation can be used, and the particular manner can be selected along with the prompt. This selection can be based on or influenced by the personality profile and/or information about the user's current context. For instance, if the user is driving, presenting an audible prompt (e.g., speech) may be preferred to a text prompt, even if the personality profile indicates a preference for text prompts.

At block 316, process 300 can assess a result of the prompt. For example, a user might act on the prompt "immediately" (e.g., beginning activity within 10 minutes of receiving the prompt). A user might act on the prompt with a delay (e.g., an hour later or two hours later). Or the user might ignore the prompt completely (e.g., does not act on the prompt within some time limit such as two hours or four hours). In some embodiments, whether the user responds to or ignores the prompt can be based on whether the user undertakes the activity recommended by the prompt; whether the user expressly acknowledges the prompt can but need not be considered.

At block 318, process 300 can update the user profile and/or the current goal based on the result at block 316. For instance, as described above, a personality profile can include scores indicative of a user's responsiveness to prompts having various characteristics, and the user's response to a given prompt (or lack of response) can be used to update the scores.

The current goal can also be updated based on the user's response. In some embodiments, goals are selected based on a heuristic algorithm and the current state of the user profile. The heuristic algorithm can be designed to set realistic goals based on knowledge of the user's personality and current activity level, and goal selection can be further informed by data gathered from numerous users over time. It should be noted that goals can be set dynamically, and it is not required that a user either achieve a goal or expressly repudiate the goal in order for a new goal to be selected. Further, goals can be defined according to different metrics; e.g., for running or walking, a goal can be expressed as a distance to cover, a destination to reach, or an amount of time to spend doing the activity. It is contemplated that different users may respond differently to different metrics, and the heuristic algorithm can experiment to find the metric to which a given user is most responsive. This information, in turn, can become part of the user's personality profile and can influence the selection of prompts as well as goals.

It will be appreciated that process 300 is illustrative and that variations and modifications are possible. Steps described as sequential may be executed in parallel, order of steps may be varied, and steps may be modified, combined, added or omitted. For instance, process 300 can continue indefinitely to gather data, select activities, and prompt the user. Process 300 can dynamically update the user profile, including the personality profile, so that over time, the content of prompts that are chosen for presentation as well as the time, place and manner of their presentation can become more likely to elicit responsive activity. Thus, the coaching system can be adaptive to a given user's personality and preferences, with the adaptation occurring automatically over time. Further, in instances where the user does not respond to a prompt, the system can address this by changing at least one characteristic of the next prompt.

Further, while process 300 is described with reference to prompting the user to engage in an activity, it is to be understood that coaching prompts can be presented during activity. In some sense, anything the user does during the day can be considered an activity, and a prompt can encourage the user to switch to a different activity (e.g., walking instead of sitting) or to continue in a current activity (e.g., keep walking) or to adjust the intensity of activity (e.g., try walking a little faster). A given user may prefer different styles for activity-switching prompts as compared to prompts to continue or adjust a current activity. Further, a user may prefer different styles for prompts associated with different types of wellness behavior (e.g., eating-related prompts versus exercise-related prompts versus sleep-related prompts). By modeling these additional dimensions within the personality profile and using them to select prompts, the coaching system can adapt itself to the user's preferences.

In some embodiments, the coaching system can make initial assumptions about the user's responsiveness, e.g., by initializing a personality profile as described above. In some embodiments, the user can be invited to provide a direct assessment of what she thinks her responsiveness would be to various coaching styles. However, users are not always the best judges of what is effective; for instance, many people tend to conflate annoying with ineffective when asked, even though this is not necessarily the case. Accordingly, the coaching system can be designed to operate initially in a "baseline" mode in which coaching prompts and presentation (time, place, manner) are selected with little or no regard for the user's personality profile. In this mode, results of prompts can be used to update the personality profile so that the profile eventually becomes reliable enough to use. In some embodiments, operation in baseline mode can continue for a fixed time, e.g., two weeks, or until such time as enough data points are gathered that the user profile becomes reliable enough to start using. In one such embodiment, the weight given to the personality profile can gradually increase over time or as data is collected until it becomes a dominant factor in selecting content, time, place, and/or manner of presentation of prompts.

As described above, in some embodiments, the coaching system can obtain initial user information by soliciting answers to specific questions, e.g., as shown in FIG. 4. In other embodiments, other sources of user information can be leveraged in addition to instead of answers to specific questions. For example, the user may have previously registered with an online service, such as an activity-tracking service provided by a gym or in connection with a personal device the user owns. In some embodiments, the coaching system can prompt the user to provide information about such registration (e.g., a username and password to access the service), after which the coaching system can communicate with the service to obtain information about the user. Information thus obtained can be used to populate a user profile. As another example, user information may be stored on one or more of a user's devices, e.g., in connection with a fitness application installed on the device. In some embodiments, the coaching system can access such stored information and use it to populate a user profile. As still another example, the coaching system can invite a new user to perform a setup sequence over the course of a day (or a few days), in which the system prompts the user to engage in various activities and monitors the user's performance. Any information gathered in the course of the setup sequence can be used to populate a user profile. Further, as described above, any information obtained for the user profile can be used to initialize the user's personality profile, regardless of the manner in which the information was obtained.

The heuristic algorithms used to select the content, time, place, and/or manner of presentation of prompts can be varied. Such algorithms can be designed such that prompts conforming to a coaching style to which the user is most responsive are presented most frequently. However, it can be useful to allow some deviation from the favored style. Such variation can draw increased attention to the prompts. Further, over time, the user's personality profile may shift, and such shifts can be detected by occasionally presenting some prompts that are not a good match to the current state of the user's profile. If the user is responsive, the personality profile can shift accordingly, and the mix of prompts that are delivered can change over time. For instance, a user may become more goal-oriented over time and may therefore become more responsive to challenge-based coaching. Or a user who has achieved a significant goal may lose interest in goals (at least for a while) and begin to prefer a more supportive or social style.

Coaching system 101 of FIG. 1 or similar systems can also provide options for the user to review data that has been gathered by the system. For instance, various user interfaces can be provided on wearable device 100 and/or host device 102 to allow the user to review previous workout data (e.g., summary of all workouts from the last week or last month) and/or current workout data (e.g., current pace during a walk or run, current heart rate, etc.). Data can be presented using numbers, graphs, animations, icons, speech, sounds, or any other technique. In some instances, the data-review interface can include controls operable by the user to initiate or interact with other coaching functions. For instance, the user may be able to view or modify a goal, or to ask for a recommended goal. The user may also be able to access additional wellness resources such as articles, demonstration videos, or the like.

Figure 6:
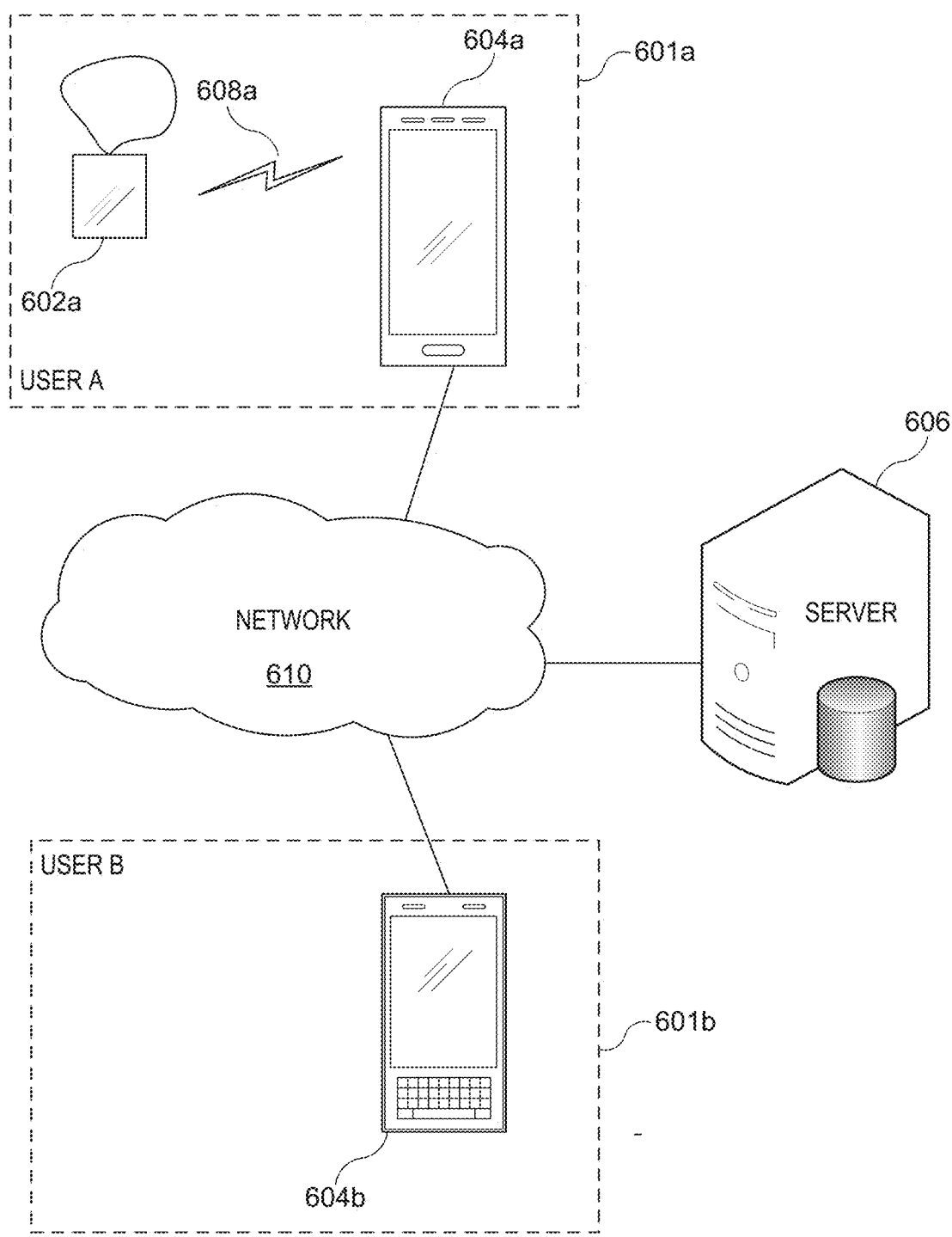
FIG. 6 shows a multi-user coaching system according to an embodiment of the present invention.

In some embodiments, the heuristic algorithms themselves can be updated, allowing the coaching system for one user to draw upon information gleaned from a larger population of users. For example, FIG. 6 shows a multi-user coaching system 600 according to an embodiment of the present invention. Coaching system 600 includes a number of personal coaching systems 601*a-b* that each include one or more personal electronic devices. For instance, personal coaching system 601*a* includes wearable device 602*a* and mobile phone device 604*a*. Coaching system 601*a* can be similar to coaching system 101 of FIG. 1, and devices 602*a* and 604*a* can communicate with each other, e.g., via a wireless communication channel 608 such as Bluetooth or the like. As another example, coaching system 601*b* includes a single device, e.g., mobile phone device 601*b*. Each personal coaching system 601*a-b* can be associated with a different user. In system 600, each personal coaching system 601 can communicate with a central coaching server 606. For example, as shown, mobile phone devices 604*a-b* in personal coaching systems 601*a-b* can communicate via network 610 (e.g., the Internet) with coaching server 606; such communication can use wired channels, wireless channels, and/or a combination thereof.

Each coaching system 601 can separately implement process 300 of FIG. 3. For example, in multi-device system 601*a*, host device 604*a* can perform initial setup (e.g., steps 302, 304, 306) and provide user profile data to wearable device 602*a*. Wearable device 602*a* can implement heuristic algorithms as described above to select prompts from a menu or library of prompts and can present the prompts, detect a response (or lack of response), and update the user profile accordingly. In other embodiments, host device 604*a* can implement the heuristic algorithms and communicate prompts to wearable device 602*a* for presentation to the user. In some embodiments, host device 604*a* can also collect user activity and context data (e.g., based on GPS data, calendar data, etc.). In any case, wearable device 602*a* can collect user activity data using its onboard sensors; such data can be shared with host device 604*a* to the extent desired. In single-device system 601*b*, host device 604*b* can implement all portions of process 300.

Although two personal coaching systems 601 are shown, it is to be understood that server 606 can communicate with a large number of personal systems 601 associated with different users. Thus, server 606 can have the ability to aggregate data about user behavior across a large number (e.g., hundreds, thousands, hundreds of thousands) of users. Such data can be used to modify the heuristic algorithms, including algorithms for selecting prompts; selecting time, place, and manner of presenting prompts; and/or setting or updating goals. Server 606 can from time to time provide updated algorithms to each personal coaching system 601, e.g., in the form of updates to the coaching application software to be executed by component devices thereof, e.g., mobile phone devices 604*a-b* and/or wearable device 602*a*.

Server 606 can also update the menu or library of prompts available to the coaching application. For instance, if a particular prompt generally meets with low responsiveness, that prompt might be retired from the library. New prompts can also be added, e.g., based on behavioral research, testing on a sample group of users, or the like.

Updates to heuristic algorithms and/or a library of prompts can be based on automated or semi-automated analysis of aggregate data across a set of users. Such analysis can include demographic elements (e.g., separately analyzing the behavior of men and women, or of users in different age groups). Further personalization can also be possible. For example, in some embodiments, updates can incorporate input from human personal trainers or coaches, who can provide insights based on their experience. In addition, in some embodiments, human trainers can provide specific updates for a particular user or group of users. For instance, the user may subscribe to receive motivation, support, and/or other information from a particular trainer, and that trainer can be personally involved in developing and updating prompts and/or algorithms for his or her subscribers.

In some embodiments, server 606 can maintain user profiles and send coaching prompts to a particular personal coaching system 601 for presentation to the user. However, if it desirable for coaching prompts to be operative without requiring network 610 connectivity, then at least some aspects of the coaching process described above can be implemented locally within personal coaching system 601.

As noted above, in some embodiments, a personal coaching system 601 can have access to the user's calendar data. Thus, for instance, system 601 can determine an activity to recommend, find a free block of time on the user's calendar during which the activity can be done, and prompt the user appropriately (e.g., based on the user's personality profile) so that the user does the activity during the free block of time.

In some embodiments, system 600 can be used coordinate activities for multiple users. For example, if user A and user B frequently go running together, A's personal system 601*a* and B's personal system 601*b* can coordinate a time to go running, e.g., by communicating via server 606 to identify a time when both users are free. Each system 601*a-b* can issue prompts based on its user's profile (which may be similar or quite different) so that the user is likely to go. As another example, system 600 can help find a time for a user to participate in a group activity such as a yoga class, e.g., by finding yoga classes that meet near the user's location at a time when the user is free. This can be accomplished without divulging details of the user's schedule to others. For example, each personal coaching system 601 can send a list of its user's free blocks of time to server 606. Server 606 can compare lists of free blocks of time for different users to find overlapping free times and inform personal coaching systems 601 of proposed times when other participants would be available.

To use social scheduling features, in some embodiments, a user can provide information to coaching system 600 identifying "activity buddies," either generally or for specific activities, and joint activities can be scheduled for any set of two or more users who all identify each other as activity buddies. Other sources of information can be used to connect users for workout purposes, e.g., lists of the user's friends or contacts on various social media services, the user's contact list, or the like.

A personal coaching system (e.g., system 101 or either of systems 601*a-b*) as described herein can engage in various combinations of data gathering and presentation to the user, providing motivational feedback, and/or goal-setting, among other functionalities. Users may differ in terms of their willingness to interact with different functionalities. Accordingly, in some embodiments, the system can operate in different modes to match the user's current comfort level with the coaching system. For instance, a user who is skeptical of the coaching system may prefer to use only the data-gathering and presentation functionalities. In a "data-only" mode, the coaching system can track the user's activity and gather data about the activity patterns; the user can access an interface (e.g., on device 100 or 102 of FIG. 1) to review the data. When presenting the data, the coaching system can offer to provide support to the user toward a general goal such as increasing her activity level.

If the user accepts this offer or is less skeptical to begin with, the coaching system can operate in a "data-motivation" mode. In this mode, in addition to gathering and presenting data, the coaching system can also provide prompts to engage in activity, e.g., as described above with reference to FIG. 3. The prompts can include prompts to change activity and/or prompts to continue or adjust a current activity.

If the user is or becomes responsive to prompts, the coaching system can operate in a "data-motivation-goals" mode. In this mode, the system can explicitly introduce a goal, which can be a system-selected goal or a goal negotiated with the user as described above, and the system can tailor its prompts toward helping the user achieve that goal. Thus, the user can choose the amount of interaction with the coaching system, and the operating model can nudge the user toward increasing her interaction over time as she experiences the benefits of adaptive wellness coaching that is tailored to her personality.

In another scenario, the user's responsiveness to coaching may deteriorate over time. In some embodiments, an adaptive coaching system that tracks user responsiveness can detect when responsiveness is deteriorating (e.g., to no response at all or to a response rate below a minimum level) and can take action aimed at increasing responsiveness. For example, the system can introduce a new feature (e.g., providing informational content or a new specific challenge for the user) or change the coaching style away from what the personality profile indicates. Such changes in style or focus may re-ignite the user's interest in continuing a fitness program.

As another example, the coaching system can prompt a user who has become less responsive or nonresponsive to define or redefine or clarify a goal, after which the coaching system can prompt the user based on the new goal. Involving the user in goal-setting may improve responsiveness.

While the invention has been described with respect to specific embodiments, one skilled in the art will recognize that numerous modifications are possible and that components, operations, and/or other features that may be described with respect to different embodiments can be incorporated into the same embodiment. Coaching systems can be implemented using one or more electronic devices including wearable and/or portable devices that can interact with each other to facilitate a variety of operations with increased convenience to the user.

A personality profile can be as simple or complex as desired. For example, a simple personality profile can assign each user to a small number of categories, e.g., four categories ranging from skeptical (collect some data, minimum prompting) to enthusiastic (collect data, prompt, and set goals). A more complex profile can include a large number of dimensions and assign scores in each dimension as described above.

Any type of wellness activity can be incorporated into a coaching system. Examples above make specific reference to exercise, but those skilled in the art will recognize that there are other aspects to wellness, such as stress management, sleep patterns, and dietary habits. Provided that a wellness coaching system can collect information regarding the user's activities in these areas, the coaching system can provide appropriate prompts, adaptively tailored to the user's personality and present status. For example, sensors in a wearable device can provide data usable to determine when the user is sleeping and to distinguish phases of sleep. Such data can be analyzed to identify potential improvements and prompt the user to alter her habits (e.g., going to bed and getting up at consistent times each day). Information about a user's eating habits can be determined, e.g., from user input indicating how much of what and when the user eats. Stress levels can be detected based on physiological sensor data, and stress-reducing activities can be suggested when the user's stress level is high, or (depending on the user's personality) the user can simply be alerted to the high stress level without a specific suggestion.

All user interfaces shown herein are also illustrative. Sizes of user interfaces or graphical elements thereof can be modified according to a particular desired form factor of a device on which the interface is presented. Icons can be used in addition to or instead of text to identify associated functions, and the number and arrangement of controls can be varied to facilitate user operation. In some embodiments, the user may be able to scroll a display, e.g., by dragging one or two fingers along the surface of a touchscreen display, to see more options than can be presented at once. Further, while the foregoing description may refer to graphical user interfaces, other interfaces can also be used. For example, an audio input interface can be provided by allowing the user to speak into a microphone of a device; the device can interpret the audio signal locally to determine a corresponding instruction or send the audio to another device for interpretation. Similarly, an audio output interface can be provided by using a speaker on a device to produce sounds. The sounds can include tones (beeps, whirrs, etc.) and/or speech sounds; for example, synthesized speech can be generated on one device and transmitted to another device as a digital audio signal, or an output device can include its own speech synthesizer.

The foregoing description may make reference to specific examples of devices such as wearable devices and/or mobile phone devices. It is to be understood that these examples are illustrative and not limiting; other devices can be substituted and can implement similar functional blocks and/or algorithms to perform operations described herein and/or other operations. It is further to be understood that different devices in a coaching system can implement different aspects of system operation. For example, in a system with a wearable device (e.g., wrist-worn device) and a second device (e.g., a mobile phone or other portable device), the wearable device can provide prompts to the user and collect user activity data (e.g., using physiological sensors, accelerometers, or the like, built into the wearable device) that can be transmitted to the second device. The initial collection of baseline information from the user, analysis of baseline information, selection of activities and prompts, and other processing operations can be performed by the second device, and the second device can provide an instruction to the wearable device as to what prompt to present. This can help reduce power consumption by the wearable device.

Embodiments of the present invention, e.g., in methods, apparatus, computer-readable media and the like, can be realized using any combination of dedicated components and/or programmable processors and/or other programmable devices. The various processes described herein can be implemented on the same processor or different processors in any combination. Where components are described as being configured to perform certain operations, such configuration can be accomplished, e.g., by designing electronic circuits to perform the operation, by programming programmable electronic circuits (such as microprocessors) to perform the operation, or any combination thereof. Further, while the embodiments described above may make reference to specific hardware and software components, those skilled in the art will appreciate that different combinations of hardware and/or software components may also be used and that particular operations described as being implemented in hardware might also be implemented in software or vice versa.

Computer programs incorporating various features of the present invention may be encoded and stored on various computer readable storage media; suitable media include magnetic disk or tape, optical storage media such as compact disk (CD) or DVD (digital versatile disk), flash memory, and other non-transitory media. Computer readable media encoded with the program code may be packaged with a compatible electronic device, or the program code may be provided separately from electronic devices (e.g., via Internet download or as a separately packaged computer-readable storage medium).

Thus, although the invention has been described with respect to specific embodiments, it will be appreciated that the invention is intended to cover all modifications and equivalents within the scope of the following claims.

What is claimed is:

1. A method of providing wellness coaching, the method comprising:
   obtaining, by an electronic coaching system comprising a host device and a wearable device, baseline information about a user, wherein the wearable device includes an input interface for receiving input from the user and one or more sensors;
   initializing, by the electronic coaching system, a personality profile for the user based at least in part on the baseline information;
   transmitting, by the electronic coaching system, the personality profile to the wearable device, wherein processing of the personality profile triggers:
      processing, by the wearable device, a first set of electrical signals detected from the one or more sensors to automatically infer user engagement in one or more wellness activities at one or more first activity times;
      identifying, by the wearable device, one or more second prompt times at which one or more previous wellness-activity prompts were presented;
      determining, by the wearable device, past responsiveness data characterizing delays between the one or more first activity times relative to the one or more second prompt times; and
      updating, by the wearable device, the personality profile to include the past responsiveness data;
   receiving, at the host device and from the wearable device, the updated personality profile that includes the past responsiveness data;
   receiving, at the host device of the electronic coaching system, a second set of electrical signals generated from the one or more sensors at the wearable device;
   determining, at the host device of the electronic coaching system, activity data associated with the user based on the second set of electrical signals generated from the one or more sensors, wherein the activity data includes an indication that the user is engaged in a physical activity;
   processing, at the host device of the electronic coaching system, the activity data to identify a wellness-related activity;
   selecting, at the host device of the electronic coaching system, a prompt to engage in the identified wellness-related activity, the prompt being selected based at least in part on the past responsiveness data of the updated personality profile;
   accessing electronic calendar data specifically associated with the user, the electronic calendar data identifying, for each appointment or event of one or more appointments or events, a time block at which the appointment or event is scheduled;
   identifying, using the electronic calendar data, an available time block during which the electronic calendar data indicates that the user is free from scheduled appointments and events;
   identifying a proposed activity time that is within the available time block;
   identifying prompt offset time based on the past responsiveness data;
   identifying a time for presentation, the time for the presentation of the prompt being the prompt offset time before a start of the proposed activity time;
   transmitting, from the host device to the wearable device, a communication that causes the wearable device to present the prompt at the identified time for presentation;
   receiving, at the host device and from the wearable device, a response to the prompt, wherein the response is inputted via the input interface of the wearable device;
   further updating the updated personality profile by assessing a responsiveness associated with the received response;
   receiving, at the host device and from the wearable device, a notification that the wearable device is not being worn by the user; and
   deactivating the one or more sensors in response to a determination that the wearable device is not being worn by the user.

2. The method of claim 1, further comprising:
   determining, by the electronic coaching system, a result of the prompt, the result including whether the user performed the identified wellness-related activity; and
   updating, by the electronic coaching system, the personality profile for the user based on the result of the prompt.

3. The method of claim 2, further comprising:
   repeatedly and iteratively performing the determining of activity data, processing the activity data to identify a wellness-related activity, selecting of a new prompt, identifying of a time for presentation, transmitting of a communication, determining a result of the prompt, and updating the personality profile.

4. The method of claim 3, further comprising:
   detecting, based at least in part on results of prompts across multiple iterations, a decreased level of responsiveness of the user to the prompts; and
   modifying the selection of a subsequent prompt to deviate from the personality profile based on the decreased level of responsiveness.

5. The method of claim 1, further comprising:
   determining, by the electronic coaching system, a goal for the user,
   wherein identifying the wellness-related activity is further based on the goal.

6. The method of claim 5, further comprising:
   determining, by the electronic coaching system, a user response to the prompt; and
   updating the goal based on the user response to the prompt.

7. The method of claim 1, wherein the past responsiveness data is further determined based at least in part on contextual information for the user, the contextual information including the electronic calendar data or a location of the user.

8. The method of claim 1 wherein the personality profile includes a plurality of scores, each score being associated with one or more characteristics corresponding to an activity prompt of the one or more previous wellness-activity prompts and indicative of a pattern of user responsiveness to the activity prompt.

9. The method of claim 1 wherein the prompt is identified by:
   selecting, based at least in part on the personality profile, a coaching style from a plurality of coaching styles; and
   identifying the prompt based at least in part on the selected coaching style.

10. The method of claim 1 wherein the second set of electrical signals includes physiological data.

11. The method of claim 1, further comprising:
   determining, for each of the one or more previous wellness-activity prompts, a type of device output used to present the previous wellness-activity prompt at the wearable device, wherein the past responsiveness data further characterizes an extent to which each of multiple types of device outputs was associated with inferred wellness-activity engagement; and
   selecting, at the host device of the electronic coaching system, a particular type of device output based on the past responsiveness data, wherein the communication causes the wearable device to present the prompt by performing a device output operation that corresponds to the particular type of device output.

12. The method of claim 1, wherein the receiving of the second set of electrical signals includes:
   receiving, at the host device and from the wearable device, a notification that the wearable device is being worn by the user.

13. An electronic coaching system including at least one computer having a processor and a memory, wherein the at least one computer is configured to:
   obtain baseline information about a user;
   initialize a personality profile for the user based at least in part on the baseline information;
   transmit the personality profile to a wearable device that includes an input interface for receiving input from the user and one or more sensors, wherein processing of the personality profile triggers:
      processing, by the wearable device, a first set of electrical signals from one or more sensors to automatically infer user engagement in one or more wellness activities at one or more first activity times, wherein a wearable device includes the one or more sensors;
      identifying, by the wearable device, one or more second prompt times at which one or more previous wellness-activity prompts were presented;
      determining, by the wearable device, past responsiveness data characterizing delays between the one or more first activity times relative to the one or more second prompt times; and
      updating, by the wearable device, the personality profile to include the past responsiveness data;
   receive, at a host device of the electronic coaching system and from the wearable device, the updated personality profile that includes the past responsiveness data;
   receive, at the host device of the electronic coaching system, a second set of electrical signals generated from the one or more sensors at the wearable device;
   determine, at the host device, activity data associated with the user based on the second set of electrical signals generated from the one or more sensors, wherein the activity data includes an indication that the user is engaged in a physical activity;
   process, at the host device, the activity data to identify a wellness-related activity;
   select, at the host device, a prompt to engage in the identified wellness-related activity, the prompt being selected based at least in part on the past responsiveness data of the updated personality profile;
   access electronic calendar data specifically associated with the user, the electronic calendar data identifying, for each appointment or event of one or more appointments or events, a time block at which the appointment or event is scheduled;
   identify, using the electronic calendar data, an available time block during which the electronic calendar data indicates that the user is free from scheduled appointments and events;
   identify a proposed activity time that is within the available time block;
   identify prompt offset time based on the past responsiveness data;
   identify a time for presentation, the time for the presentation of the selected prompt being the prompt offset time before a start of the proposed activity time;
   transmit, from the host device to the wearable device, a communication that causes the wearable device to present the prompt at the identified time for presentation;
   receive, at the host device and from the wearable device, a response to the prompt, wherein the response is inputted via the input interface of the wearable device;
   further update the updated personality profile by assessing a responsiveness associated with the received response;
   receive, at the host device and from the wearable device, a notification that the wearable device is not being worn by the user; and
   deactivate the one or more sensors in response to a determination that the wearable device is not being worn by the user.

14. The electronic coaching system of claim 13, wherein the at least one computer comprises a computer implemented in the host device, and wherein the host device includes a portable device.

15. The electronic coaching system of claim 14, wherein the electronic coaching system further includes the wearable device.

16. The electronic coaching system of claim 15, wherein the second set of electrical signals includes physiological data.

17. The electronic coaching system of claim 15, wherein the host device includes a user interface and the at least one computer is further configured to obtain at least some of the baseline information about the user via the user interface of the host device.

18. The electronic coaching system of claim 13, wherein the at least one computer is further configured to:
   determine, for each of the one or more previous wellness-activity prompts, a type of device output used to present the previous wellness-activity prompt at the wearable device, wherein the past responsiveness data further characterizes an extent to which each of multiple types of device outputs was associated with inferred wellness-activity engagement; and
   select, at the host device, a particular type of device output based on the past responsiveness data, wherein the communication causes the wearable device to present the prompt by performing a device output operation that corresponds to the particular type of device output.

* * * * *

UNITED STATES PATENT AND TRADEMARK OFFICE
CERTIFICATE OF CORRECTION

| | | |
|---|---|---|
| PATENT NO. | : 11,056,238 B1 | Page 1 of 1 |
| APPLICATION NO. | : 14/670846 | |
| DATED | : July 6, 2021 | |
| INVENTOR(S) | : Taido L. Nakajima, Bryan J. James and Barker N. Bhaskaran | |

It is certified that error appears in the above-identified patent and that said Letters Patent is hereby corrected as shown below:

In the Claims

Column 24, Claim 13, Line 21 delete "identifying prompt offset" and insert --identifying a prompt offset--.

Signed and Sealed this
Tenth Day of August, 2021

Drew Hirshfeld
*Performing the Functions and Duties of the*
*Under Secretary of Commerce for Intellectual Property and*
*Director of the United States Patent and Trademark Office*